United States Patent
Lu et al.

(10) Patent No.: US 9,064,965 B2
(45) Date of Patent: Jun. 23, 2015

(54) ZINC OXIDE-BASED THIN FILM TRANSISTOR BIOSENSORS WITH HIGH SENSITIVITY AND SELECTIVITY

(71) Applicant: Rutgers, The State University of New Jersey, New Brunswick, NJ (US)

(72) Inventors: Yicheng Lu, East Brunswick, NJ (US); Pavel Ivanoff Reyes, Mountainside, NJ (US); Ki-Bum Lee, Monmouth Junction, NJ (US); Aniruddh Solanki, South Plainfield, NJ (US); Chieh-Jen Ku, Edison, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 56 days.

(21) Appl. No.: 13/776,703

(22) Filed: Feb. 25, 2013

(65) Prior Publication Data

US 2013/0221346 A1  Aug. 29, 2013

Related U.S. Application Data

(60) Provisional application No. 61/602,844, filed on Feb. 24, 2012.

(51) Int. Cl.
*H01L 29/786* (2006.01)
*G01N 27/414* (2006.01)

(52) U.S. Cl.
CPC ........ *H01L 29/7869* (2013.01); *G01N 27/4145* (2013.01)

(58) Field of Classification Search
CPC ..................................... H01L 29/7869
USPC ............................. 257/43, E29.068
See application file for complete search history.

(56) References Cited

U.S. PATENT DOCUMENTS

| | | | |
|---|---|---|---|
| 6,914,279 B2* | 7/2005 | Lu et al. | 506/39 |
| 7,309,621 B2* | 12/2007 | Conley et al. | 438/99 |
| 7,544,967 B2* | 6/2009 | Kim et al. | 257/40 |
| 7,759,710 B1* | 7/2010 | Chiu et al. | 257/253 |
| 7,989,851 B2* | 8/2011 | Lu et al. | 257/252 |
| 8,632,969 B2* | 1/2014 | Shim et al. | 435/6.1 |
| 2009/0068755 A1* | 3/2009 | Steeves et al. | 436/172 |
| 2010/0244017 A1* | 9/2010 | Hoffman et al. | 257/43 |

OTHER PUBLICATIONS

Bergveld, "Development of an Ion-Sensitive Solid-State Device for Neurophysiological Measurements," IEEE Trans Biomed Eng., (1970) vol. BME-17, pp. 70-71 (Abstract only).

(Continued)

*Primary Examiner* — Lex Malsawma
(74) *Attorney, Agent, or Firm* — Fox Rothschild LLP

(57) ABSTRACT

This application discloses ZnO film transistor-based immunosensors (ZnO-bioTFT), 2T biosensor arrays formed from two integrated ZnO-bioTFTs, 1T1R-based nonvolatile memory (NVM) arrays formed from ZnO-bioTFT (T) integrated with ZnO-based resistive switches (R), as well as integrated bioTFT (IBTFT) sensor systems formed from 2T biosensor arrays and 1T1R NVM arrays. Through biofunctionalization, these biosensors can perform immunosensing with high sensitivity and selectivity, and therefore have a wide range of applications, for example, in detecting target biomolecules or small molecules, and potential application in cancer diagnosis and treatment.

20 Claims, 12 Drawing Sheets

(56) References Cited

OTHER PUBLICATIONS

Ebisawa et al., "Electrical properties of polyacetylene/polysiloxane interface," J. Appl. Phys., (1983) vol. 54, pp. 3255-3259 (Abstract only).
Ku et al., "Effects of Mg on the Electrical Characteristics and Thermal Stability of $Mg_xZn_{1-x}O$ Thin Film Transistors," Appl. Phys. Lett., (2011) vol. 98, p. 123511.
Estrela et al., "Field Effect Detection of Biomolecular Interaction,", Electrochimca Acta (2005) vol. 50, pp. 4995-5000 (Abstract only).
Gimmel et al., "Microstructured solid-state ion-sensitive membranes by thermal oxidation of Ta," Sens. Actuators B, (1990) vol. 1, pp. 345-349 (Abstract only).
Hsueh et al., "Highly sensitive ZnO nanowire ethanol sensor with Pd adsorption," Appl. Phys. Lett, (2007) vol. 91, p. 053111 (Abstract only).
Mabeck et al., "Chemical and biological sensors based on organic thin-film transistors," Anal. Bioanal. Chem., (2006) vol. 384, pp. 343-353 (Abstract only).
Reyes et al., "A ZnO nanostructure-based quartz crystal microbalance (QCM) for selective biochemical sensing applications," IEEE J. Sens, (2009) vol. 10, p. 2030250 (Abstract only).
Torsi, "Multi-parameter gas sensors based on organic thin-film-transistors," Sens. Actuators B, (2000), vol. 67, pp. 312-316 (Abstract only).
Wei et al., "Enzymatic glucose biosensor based on ZnO nanorod array grown by hydrothermal decomposition," Appl. Phys. Lett, (2009), vol. 89, p. 123902.
Yu et al., "AlGaN/GaN heterostructures for non-invasive cell electrophysiological measurements," Biosens. Bioelectron., (2007) vol. 23, pp. 513-519 (Abstract only).
Zhang et al., "DNA hybridization detection with organic thin film transistors: toward fast and disposable DNA microarray chips," Biosens Bioelectron, (2007) vol. 22, pp. 3182-3187 (Abstract only).
Zhang et al., IEEE Trans. Ultrason Ferroelectr Freq Contr., (2006) vol. 53(4), pp. 786-792 (Abstract only).
Zhang et al., "Fast and Reversible Wettability Transitions on ZnO Nanostructures," J. Electr. Mat., (2007) vol. 36(8), pp. 895-899 (Abstract only).
Zhang et al., "FeZnO based resistive switch devices," Journal of Electronic Materials, (2012) vol. 41, pp. 2880-2885 (Abstract only).

* cited by examiner

FIGURES 5 A-D
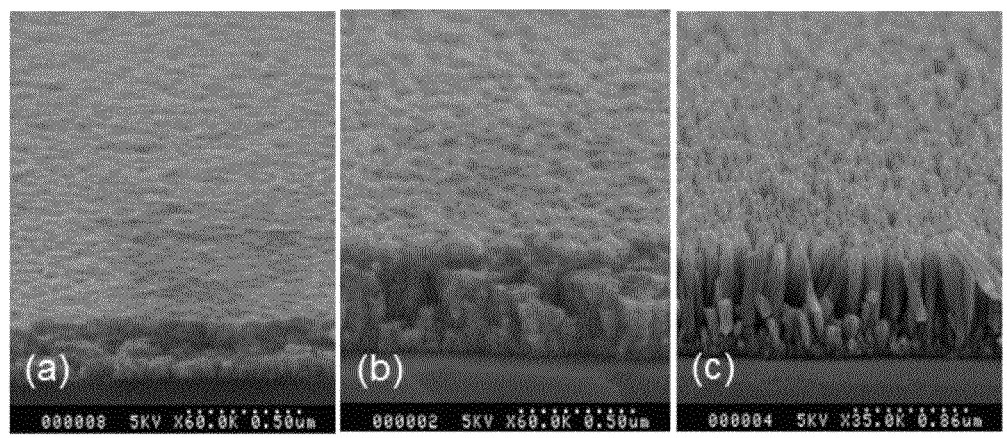
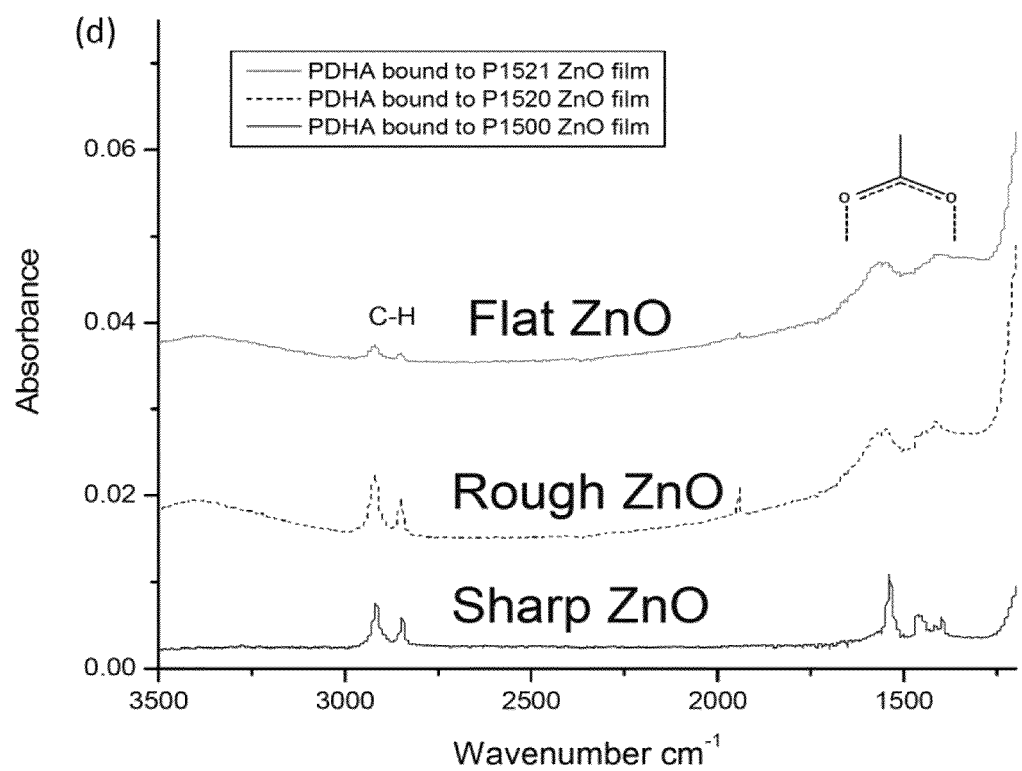

FIGURES 7 A-B

ZINC OXIDE-BASED THIN FILM TRANSISTOR BIOSENSORS WITH HIGH SENSITIVITY AND SELECTIVITY

CROSS REFERENCE TO RELATED APPLICATIONS

This application claims priority under 35 U.S.C. §119(e) to U.S. Provisional Patent Application Ser. No. 61/602,844, filed on Feb. 24, 2012, which is hereby incorporated by reference in its entirety.

STATEMENT REGARDING FEDERALLY FUNDED RESEARCH

The research leading to the present invention was supported at least in part by AFOSR under FA9550-08-01-0452 and by the NSF under ECCS 1002178. Accordingly, the U.S. Government has certain rights in this invention.

FIELD OF THE INVENTION

The present invention relates generally to sensors. More particularly, the present invention discloses zinc oxide thin film transistor-based biosensor (ZnO-bioTFT) systems.

BACKGROUND OF THE INVENTION

The field-effect transistor (FET) has been used as biochemical sensors since the first introduction of the ion-selective field effect transistors (ISFET) in 1970, See, for example, P. Bergveld, *IEEE Trans. Biomed Eng.* 17, 70, (1970), The basic structure of an ISFET comprises an insulator-semiconductor junction FET with a non-metallized gate serving as the sensor where the analyte solution is sensed. ISFET devices have been used popularly as a sensitive pH sensor and various biochemical sensors. See, for example, P. Begveld, *Sens. Actuators B* 88, 1-20, (2003).

Since then, the development of more sensitive versions of the ISFET has been geared towards the selection of the inorganic material used for the non metallized gate such as $Si_3N_4$ and $Ta_2O_5$. See, for example, M. Asahi, and T. Matsuo, *Suppl. Jpn. Soy, Appl. Phys.* 44, 339, (1975); P. Gimmel, K. D. Schierbaum, Gopel, H. H. Van den Vlekkert, and N. F. deRooy, *Sens. Actuators B* 1, 345, (1990).

More recently the biosensing ISFET mechanism has been applied to Poly-Si thin film transistors (TFTs) and GaN/AlGaN high electron mobility transistors (HEMTs) for detection of DNA, penicillin, and cellular potentials. See, for example, P. Estela, A. G. Stewart, F. Yan, and P. Migliorato, *Electrochimca Acta* 50, 4995-5000, (2005); J. Yu, S. K. Jha, L. Xiao, Q. Liu, P. Wang, C. Surya, and M. Yang, *Biosens. Bioelectron.* 23, 513-519, (2007). However, the entire gate of this type of devices serves as the sensing area which contains the analyte solution. The biasing of the ISFET can be invasive as it is done by using a reference electrode dipped directly into the analyte on the gate oxide. This configuration may also disturb the solution being detected, especially if the bias is too high.

Another class of FET-type of biosensors is based on organic field-effect transistors (OFETs), which are usually fabricated at low temperatures on various substrates including glass and flexible polymers. The general structure of an OFET includes a back-gate MOSFET with the conducting channel, made of organic semiconductors. The analyte can be in any of three locations on the exposed organic channel as in the case of gas sensors, or between the insulator and gate layers as in the case of ion sensitive sensors (pH sensors), or the analyte can act as the insulator itself between the organic semiconductor and the gate, as in the case of the electrochemical sensors. See, for example, J. T. Mabeck1, and G. G. Malliaras, *Anal. Bioanal. Chem.* 384, 343-353, (2006). Since the first OFET was introduced, research efforts in OFET biochemical sensors have focused on development of various organic semiconductors to increase the device's sensitivity and selectivity in detecting wide range of chemicals including gases, enzymes, and DNA. See, for example, F. Ebisawa, T. Kurokawa. S. Nara, *J. Appl. Phys.* 54, 3255-3259, (1983); L. Torsi, A. Dodabalapur, L. Sabbatini, and P. G. Zambonin, *Sens. Actuators B* 67, 312-316, (2000); J. Liu, M. Agrawal, and K Varahramyan, *Sens. Actuators B* 135, 195 199, (2008); Q. Zhang, and V. Subramanian, *Biosens. Bioelectron.* 22, 3182-3187, (2007). The OFET has the advantage of being easily controlled through biasing due to the back-gate configuration. However, the level of bias voltage required to operate OFETs is generally high, which could cause unwanted electrochemical reactions during, testing. Furthermore, the OFETs have low mobility and on-off ratios under the normal voltage biasing, The low output current levels lead to small signal to noise ratios, making the sensors susceptible to noise.

Currently, nanowire-based FET sensors are demonstrated with high sensitivity reaching the order of fM. See, for example, K. S. Chang, C. C. Chen. J. T. Sheu, and Y.-K. Li, *Sens, Actuators B* 138, 148-153, (2009). However, these prototypes of sensors generally involve a complex fabrication process as they are constructed individually by manipulating and aligning a single strand of semiconducting nanowire such as $TiO_2$ or Si as the FET channel between the source and drain patterns. It is difficult to achieve repeatability and manufacturability in fabrication and integration of these devices for larger sensor arrays.

ZnO is emerging as a wide handgap semiconductor oxide with multifunctional properties that makes it an attractive sensor material. ZnO is highly sensitive to various molecules including $CH_4$, CO, $H_2O$, $H_2$, $NH_3$, trimethylamine, ethanol and $NO_2$. See, for example, V. I. Anisimkin, M. Penza, A. Valentini, F. Quaranta, and L. Vasanelli, *Sens Actuators B* 23, 197. (1995); T.-J. Hsueh, S-J. Chang, C-L. Hsu, Y-R. Lin, I-C. Chen, *Appl. Phys. Left,* 91, 053111 (2007). ZnO and its nanostructures are compatible with intracellular material and ZnO-based sensors have been demonstrated for detection of biochemicals such as enzymes, antibodies, DNA immobilization and hybridization. See, for example, S. M. Al-Hilli, R. T. Al-Mofarji, and M. Willander, *Appl. Phys. Lett.* 89, 17, 173119 (2006); A. Wei, X. W. Sun, J. X. Wang, Y. Lei, X, P. Cai, C. M. Li, Z. L. Dong, W. Huang, *Appl. Phys. Lett,* 89, 12, 123902. (2006); P. I. Reyes, Z. Zhang, H. Chen, Z. Duan, J. Zhong, G, Saraf, Y. Lu, O. Taratula, E. Galoppini, N. N. Boustany, *IEEE J. Sens,* 10, 2030250, (2009); Z. Zhang, N. W. Emanetoglu, Saraf, Y. Chen, P. Wu, J. Zhong, Y. Lu, J. Chen, O. Mirochnitchenko, M. Inouye, *IEEE Trans. Ultrasonics, Ferroelect. Freq. Contr.* 53, 4, 786-792, (2006).

Accordingly, there is an immediate need for improved sensors and sensing methods.

SUMMARY OF THE INVENTION

The present invention was designed to meet the foregoing need by providing a variety of ZnO film transistor-based biosensors with high sensitivity and selectivity.

In one embodiment, the present invention provides a zinc oxide based thin film transistor biosensor (ZnO-bioTFT sensor), in which a ZnO-based thin film transistor (TFT) is built on a substrate, wherein the ZnO-TFT has a bottom-gate TFT, and the bottom-gate TFT has an exposed top channel layer made from a ZnO-based material In another embodiment, the present invention provides a 2T biosensor array comprising a 2T basic cell formed from a ZnO-bioTFT sensor integrated with a second TFT.

In another embodiment, the present invention provides a 1T1R-based nonvolatile memory (NVM array, comprising a ZnO-bioTFT (T) and a ZnO-based resistive switch (R), wherein the ZnO-TFT (T) and the ZnO-based resistive switch (R) are integrated to form a ZnO-based 1T1R basic unit cell configurations.

In another embodiment, the present invention provides an integrated bioTFT (IBTFT) sensor system, comprising a 2T biosensor array formed from a ZnO-bioTFT sensor integrated with a second TFT, and a 1T1R NVM array formed from a ZnO-bioTFT (T) integrated with a ZnO-based resistive switch (R), wherein the 2T biosensor array and the 1T1R NVM array form an integrated system with a built-in data storage.

Through biofunctionalization, these biosensors can perform immunosensing with high sensitivity and selectivity, and therefore have a wide range of applications, for example, in detecting target biomolecules or small molecules, and potential application in cancer diagnosis and treatment.

The back-gate TFT can have an on-off ratio of $10^8$ and a threshold voltage of 4.25 V. The ZnO channel surface can be biofunctionalized with primary monoclonal antibodies that selectively bind with epidermal factor receptor (EGFR). Detection of the antibody-antigen reaction is achieved channel carrier modulation via pseudo double-gating field effect caused by the biochemical reaction. The sensitivity of a 10 fM detection of pure EGFR proteins can be achieved. The ZnO-bioTFT immunosensor can also selectively detect 10 fM of EGFR in a 5 mg/ml goat serum, containing various other proteins.

These and other aspects of the present invention will be better appreciated in view of the following drawings, detailed description, and claims.

BRIEF DESCRIPTION OF THE DRAWINGS

FIG. 5 illustrates optimized DNA binding through morphology control of ZnO nanostructures. FESEM images of the MOCVD-grown ZnO films on glass with different morphologies: (a) Flat surface, (b) Rough surface, (c) Sharp surface. (d) FTIR spectra of binding DNA on ZnO Films;

DETAILED DESCRIPTION OF THE INVENTION

The present invention provides, inter alia, highly sensitive and selective immunosensing ZnO-based thin film transistor biosensors (ZnO-bioTFTs). Epidermal growth factor receptor (EGFR) is used as an example because the sensing of EDFR-antibodies reacting with EGFR proteins has its implications in cancer related studies and drug screening for cancer, as EGFR is well-known to be over-expressed in solid tumors, especially breast cancers. It will be appreciated, however, the instant invention need not be so limited. Embodiment ZnO-bioTFT devices possess excellent and repeatable characteristics. Various embodiment devices can be integrated into a large scale device at low cost, which provides benefits for the further development of a platform not only for diagnosing cancers but also for monitoring a patient's response to therapy in real-time by monitoring changes in the levels of biomarkers within the patient's serum.

Figure 11:
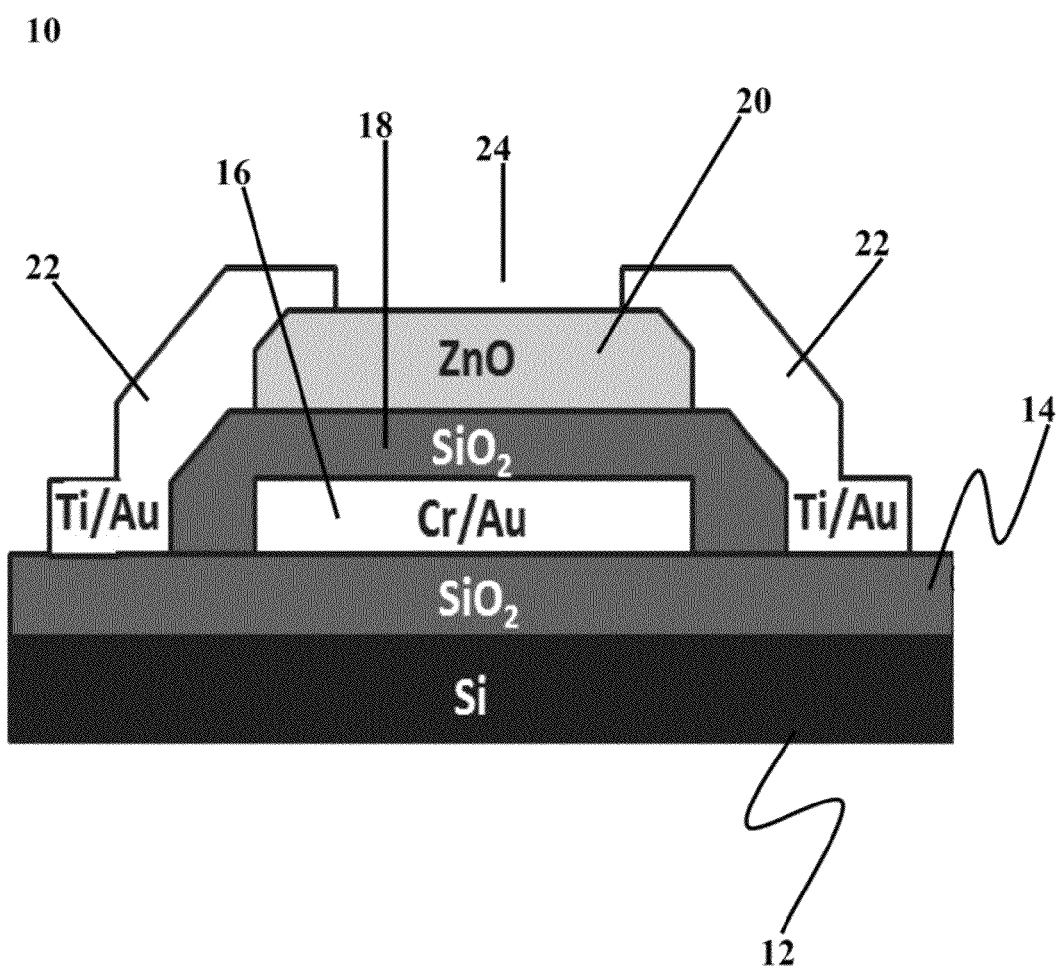
FIG. 11 is a side view of an embodiment device according to the present invention.
Figure 12:
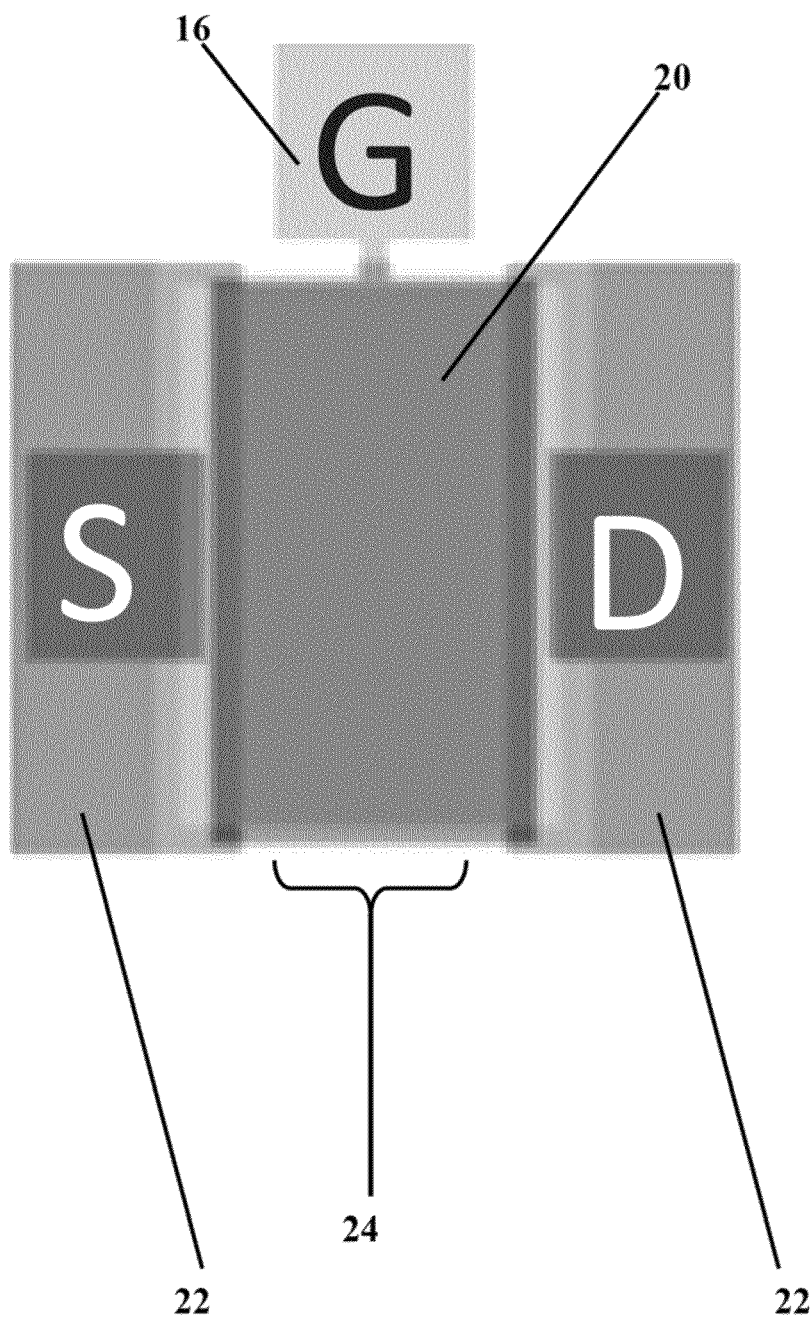
FIG. 12 is a top view of the FIG. 11 device.

An embodiment device schematic is shown FIG. 11. The embodiment device 10 follows a back-gate inverted-staggered configuration. A Si substrate 12 can be covered with a 1 pm layer 14 of $SiO_2$ through, for example, wet oxidation followed by e-beam deposition of, for example, a layer 16 of Au (50 nm)/Cr (100 nm) that serves as the gate electrode. A 70 nm layer 18 of $SiO_2$ can then be grown through plasma enhanced chemical vapor deposition (PECVD) as the gate oxide layer. A 50 nm ZnO thin film 20 can be grown using metalorganic chemical vapor deposition (MOCVD) on top of the $SiO_2$ to serve as an n-type conduction channel. Au (50 nm)/Ti (100 nm) layer 22 can be deposited through electron-beam evaporation for the source and drain Ohmic contacts. The exposed ZnO channel 24 can act as the sensing area and can have, for example, a dimension of 200 μm×400 μm, giving a W/L ratio of 2. Shown in FIG. 12 is a top view of the TFT device of FIG. 11.

Figure 1:
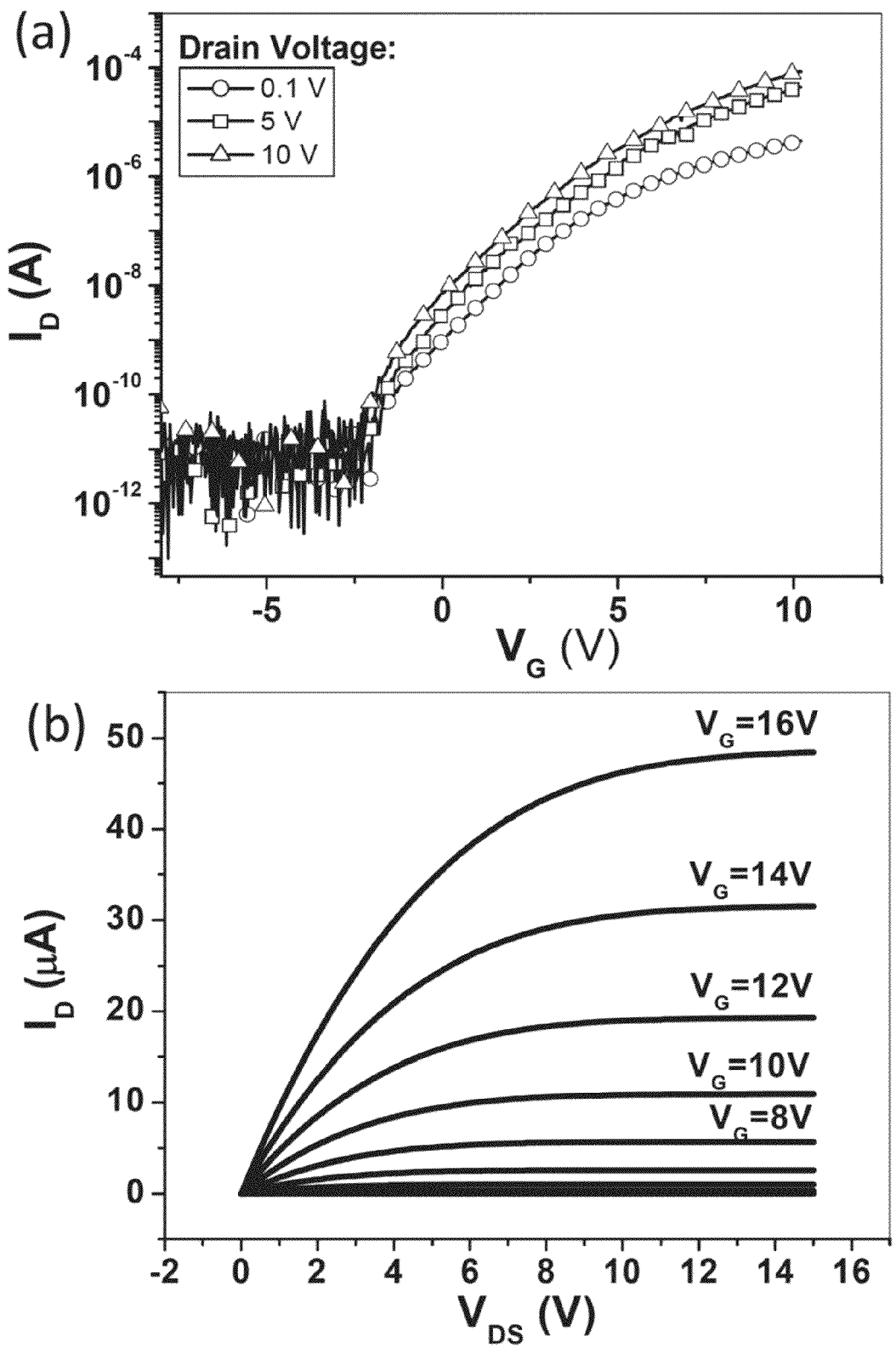
FIG. 1A illustrates a transconductance curve of an embodiment ZnO-bioTFT and its vertical structure schematic (inset)
FIG. 1B illustrates embodiment transistor characteristic curves for various gate bias, and the top view of the device (inset)
Figure 2:
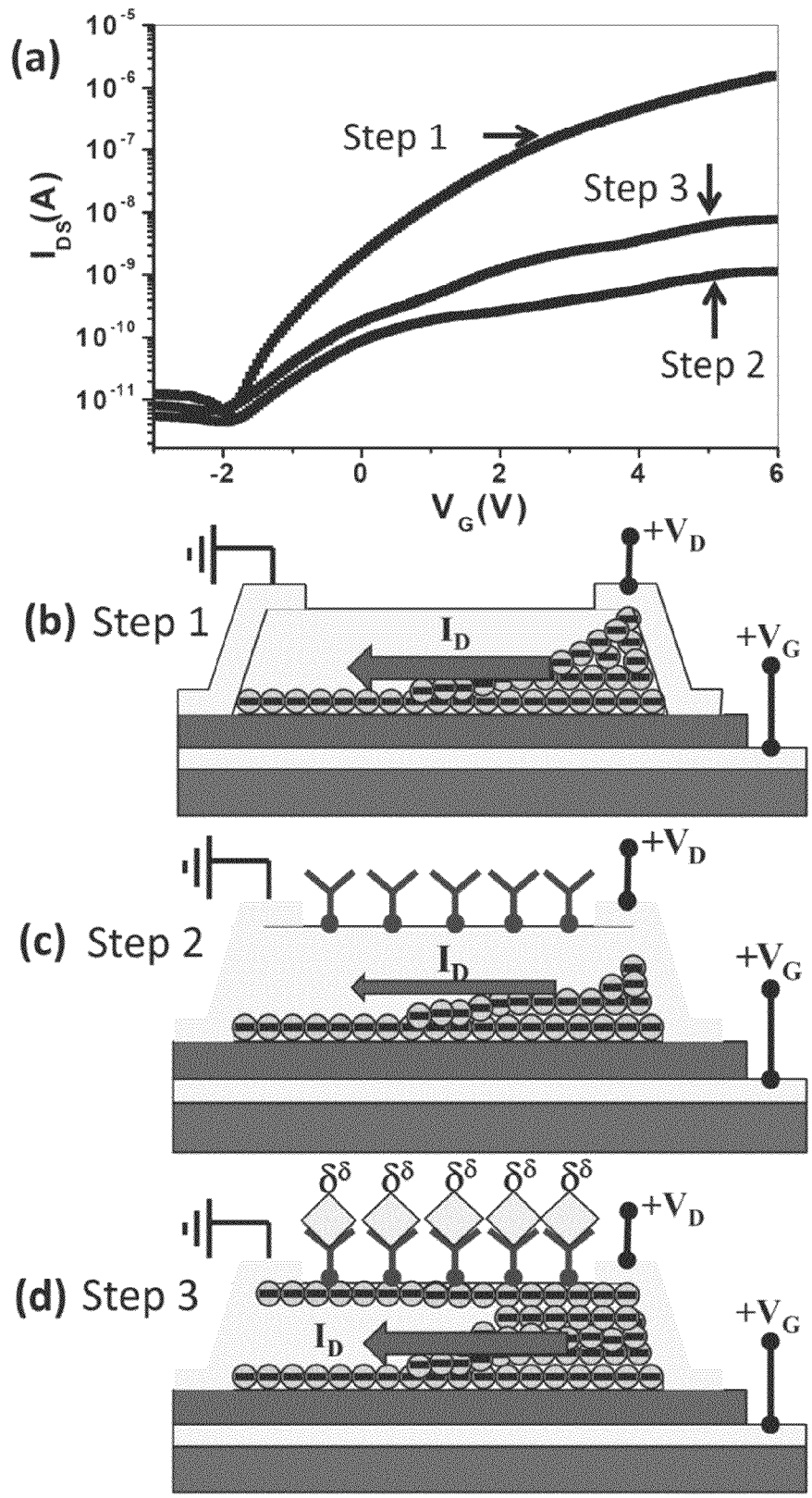
FIG. 2 illustrates drain current versus gate bias for fixed drain bias of 10V in an embodiment device, in which step 1 illustrates a bare device, step 2 illustrates EGFR-antibody immobilization and step 3 illustrates EGFR protein detection, and in which (b)-(d) are schematic diagrams of the carrier modulation mechanism for steps 1 to 3, respectively.

The electrical characteristics of an embodiment ZnO-bioTFT are shown in FIGS. 1A-1B. The transconductance curve (drain current ($I_D$) vs. gate voltage ($V_{GS}$)) in FIG. 1A shows that the embodiment bioTFT is a normally-OFF enhancement mode transistor with a threshold voltage of 4.25 V and an ON-OFF ratio of The high ON-OFF ratio of the device provides the high sensitivity of the device to the charge modulation within the ZnO channel. FIG. 2(b) shows the transistor characteristic curves with drain current versus drain voltage for various gate-biasing of the embodiment device.

Thus, in one embodiment, the present invention provides a zinc oxide thin film transistor-based biosensor (ZnO-bioTFT sensor), comprising a ZnO-based thin film transistor (TFT) built on a substrate, wherein the ZnO-TFT comprises a bottom-gate TFT, and the bottom-gate TFT comprises a channel layer made from a ZnO-based material; and wherein the TFT channel layer is biofunctionalized.

In another embodiment, the ZnO-bioTFT sensor of the present invention has a pseudo double-voting effect. In another embodiment of the ZnO-bioTFT sensor of the present invention, the ZnO-based channel layer is exposed to biospecies. In another embodiment of the ZnO-bioTFT sensor of the present invention, the substrate is a solid-state state or flexible material. In another embodiment of the ZnO-bioTFT sensor of the present invention, the substrate is selected from silicon, glass, and polymers.

In another embodiment of the ZnO-bioTFT sensor of the present invention, the ZnO-based material is a pure or doped-ZnO film. In another embodiment of the ZnO-bioTFT sensor of the present invention, the ZnO-based material is further modified by growing ZnO-based nanostructures with controlled surface morphology and wettability on top of the films.

In another embodiment of the ZnO-bioTFT sensor of the present invention, the ZnO-based nanostructures have the controlled surface wettability so that the super hydrophilicity of the surface reduces liquid sample consumption and significantly enhances the sensitivity of the TFT sensor, In another embodiment of the ZnO-bioTFT sensor of the present invention, the ZnO-based nanostructures have the controlled morphology, selected from flat, rough, and sharp tip end, to enhance the binding affinity with different bio-species and enhance the sensitivity and selectivity of the TFT sensor.

In another embodiment of the ZnO-bioTFT sensor of the present invention, the ZnO-based material comprises pure and doped $Mg_xZn_{1-x}O$ (x<0.06) (MZO) films. In another embodiment of the ZnO-bioTFT sensor of the present invention, the MZO-based material is further modified with depositing MZO-based nanostructures with controlled surface morphology and wettability on top of the films.

In another embodiment of the ZnO-bioTFT sensor of the present invention, the MZO-based nanostructures have the controlled surface wettability so that the super-hydrophilicity of the surface reduces liquid sample consumption and significantly enhances the sensitivity of the TFT device. In another embodiment of the ZnO-bioTFT sensor of the present invention, the MZO-based nanostructures of the TFT device have the controlled morphology, selected from flat, rough, and sharp tip end, to enhance the binding with different bio-species and enhance the sensitivity and selectivity of the TFT sensor.

In another embodiment of the ZnO-bioTFT sensor of the present invention, the MZO-based material is stable in a wide range of pH levels, thus increasing the number of biochemical types that the sensor can detect, and improving the sensor fabrication process in which wet chemicals are involved. In another embodiment of the ZnO-bioTFT sensor of the present invention, the biofunctionalization comprises a flexible chemical functionalization method that can be applied to different types of specific biochemical detection, and enhances the selectivity of the biosensor. In another embodiment, the present invention provides a 2T biosensor array comprising a 2T basic cell formed from a ZnO-bioTFT sensor according to any one of the embodiments as described above, integrated with a second TFT.

In another embodiment, the present invention provides a 2T biosensor array capable of multimode sensing operations, including, but not limited to, electrical mode and optical mode. In another embodiment, the present invention provides a 2T biosensor array, wherein the sensing operation in electrical mode comprises outputting electrical characteristics from said 2T biosensor array; and wherein the sensing operation in optical mode comprises outputting fluorescence imaging from said 2T biosensor array.

In another embodiment, the present invention provides a 1T1R-based nonvolatile memory (NVM) array, comprising a ZnO-bioTFT (T) and a ZnO-based resistive switch (R), wherein the ZnO-TFT (T) and the ZnO-based resistive switch (R) are integrated to form a ZnO-based 1T1R basic unit cell configuration. In another embodiment, the present invention provides an integrated bioTFT (IBTFT) sensor system, comprising, a 2T biosensor array formed from a ZnO-bioTFT sensor according to any of the embodiments described above integrated with a second TFT, and a 1T1R NVM array formed from a ZnO-bioTFT (T) according to any of the embodiments described, above integrated with a ZnO-based resistive switch (R), wherein the 2T biosensor array and the 1T1R NVM array form an integrated system with a built-in data storage.

Wettability Control of Sensing Surfaces:

One of the unique properties of ZnO and MZO is controllable surface wettability, which could greatly benefit the biosensing. ZnO nanostructures exhibit reversible hydrophilic and hydrophobic states in fast transitions. The superhydrophilic state is attained by UV exposure and the superhydrophobic state is attained by oxygen annealing as shown in our previous results (see Zhang, Z., Chen, H., Zhong, J., Saraf, G., and Lu, Y., *TMS & IEEE J. Electr. Mat.*, 36, 8, 895. (2007)). The invention utilizes enhanced growth and doping processes and optimized surface treatment to achieve the better and faster wettability control. We are particularly interested in the superhydrophilic state because it only requires a percent of the liquid consumption to fill an equal area of a normal sensing surface.

Morphological control of Sensing Surface:

The size of the target molecule also affects the extent of binding to the ZnO and MZO nanostructures. This can be optimized by tuning the surface morphology of the nanostructures as shown in FIG. 5. The results in FIG. 5 indicate the enhanced attachment of DNA molecules for sharp surface morphology. The invention utilizes the growth optimization and the results of the effects of surface morphology of the MZO nanostructures to the various biochemical species being detected.

The invention is not limited to the use of ZnO as the transistor channel. The sensor also uses the alloy $Mg_xZn_{1-x}O$ (MZO) instead of the pure ZnO as both of the TFT channel and the nanostructured sensing layer. This is mainly due to (i) the larger range of pH that $Mg_xZn_{1-x}O$ can handle and (ii) the higher reliability when used as the TFT channel layer. Specifically for the invention the TFT will have $Mg_xZn_{1-x}O$ (0<x<0.06) for the MZO bioTFT technology.

For sensor applications, stability against environmental changes is required. Any deviation of electrical characteristics induced by TFT instability will affect the operation region and sensitivity of individual sensors. The use of MZO instead of the pure ZnO for the TFT will significantly enhance thermal stability and negative bias stress stability. It is known that electrical characteristics of oxide based TFTs are largely dependent on intrinsic defects. Among them, the oxygen vacancy has been widely accepted as the most important factor to determine oxide TFT performance and instability. The MZO TFT technology utilizes the fact that Mg—O possesses higher bonding energy than that of Zn—O, therefore, increasing the formation energy of the oxygen vacancy in MZO TFTs. $O_{1s}$ peaks in XPS spectra indicates that oxygen vacancy related defects is suppressed after incorporation of Mg into ZnO to form MZO channel layer (See Chieh-Jen Ku, Ziqing Duan, Pavel Ivanoff Reyes, and Yicheng Lu, Yi Xu, Chien-Lan Hsueh and Eric Garfunkel, *Appl. Phys. Lett.* 98, 123511, 2011.) With ~6% Mg incorporation into a ZnO channel, the field effect mobility and subthreshold swing, values are improved. A smaller (negative) shift of threshold voltage and higher activation energy are observed. The improved electrical characteristics and thermal stability of $Mg_{0.06}Zn_{0.94}O$ TFT are mainly attributed to the suppression of oxygen vacancies by introducing stronger Mg—O bonding in the channel layer.

The enhancement of negative bias stability (NBS) in MZO TFTs is mainly attributed to the strengthened atomic bonding after introduction of a small Mg composition into ZnO, leading to the suppression of oxygen vacancies. Recently, IGZO TFT technology has attracted increasing interest particularly for the advanced display technology. However, for the large-area biosensing systems, the high performance and stable MZO TFT technology without using Indium could offer the important advantages, including the low cost, safety to environment, and biocompatibility.

MZO also broadens the energy band gap over ZnO, which benefits for the optical, mode sensing. As most biochemical materials have unique absorption characteristics in the UV-visible spectrum, such as 260-370 nm, the activity at reaction surfaces of a MZO bioTFT sensor would allow for identification of the bin species present. This added mode of operation will enable us to use the same bioTFT sensor array platform for benchmarking, the device with standard techniques. This makes the biosensors extendable to optical modes of operation by detecting the Changes in optical absorption and fluorescence characteristics before and after bin-reactions.

To realize the immunosensing ability of the ZnO-bioTFT, the exposed ZnO channel, can be functionalized using linkage chemistry, which typically involves three basic steps. By way of example, the following steps may be performed, although other steps can be possible to provide for the sensing of another analyte. First, the ZnO channel can be functionalized with trimethoxysilane aldehyde (having a reactive aldehyde end group) by incubating the device in 1% v/v solution of silane-aldehyde in 95% ethanol for 30 min. The device can then be cured, for example, in an oven at 120° C. for 15 min. Second, the aldehyde groups can be coupled to the amine groups of for example, monoclonal EGFR antibodies (1:50) through reductive amination in the presence of 4 mM sodium. cyanoborohydride in PBS (pH 7.4) for two hours. Third, unreacted aldehyde groups can be blocked using 100 mM ethanolamine in a similar manner to prevent non-specific interactions of proteins. Finally, the device can be rinsed in a continuous flow of PBS, pH 7.4 for 1.0 min.

The flexibility of the chemical functionalization method used in the invention makes the device useful for attaching essentially any ligand having an affinity for a biomarker, Examples of biomarkers for which ligands having affinity therefor may be attached to the exposed ZnO channel include, but are not limited to DNA, oligo-nucleotides, proteins, biotin, streptavidin, and the like. Protein ligands include monoclonal antibodies (mABs); however enzyme substrates may also be used as ligands having affinity for a corresponding enzyme.

According to one embodiment, the exposed ZnO channel is functionalized with monoclonal antibodies by means of a reactive amino group on the mAB. Because most antibodies have lysine groups, they can be attached to the device at the lysine amino group. In this manner, the device can be functionalized with mABs against prostate specific antigen (PSA) to detect the presence of PSA in a patient's serum suffering from or at risk for prostate cancer.

Furthermore, the device is not limited to being used only for detecting cancer biomarkers, but can also be used for various other conditions. The chemical functionalization method also enables the bioconjugation of DNA aptamers having an amino group. These aptamers could potentially bind small molecules and proteins. Once bound, the change in the charge on the surface of ZnO would enable the device to detect the target biomolecule or small molecule). The invention has already been demonstrated to be highly sensitive for detecting cancer biomarkers. In addition, the device is highly selective as it detected biomarker concentrations in the femtomolar (fM) range in the presence of high amounts of goat serum (5 mg/ml), which consists of a high concentration of various other proteins.

The term "functionalization" or "chemical functionalization," as used herein, means addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term "biofunctionalization," "biofunctionalized," or the like, as used herein, means modification of the surface of a material so that it has desired biological function, which will be readily appreciated by a person of skill in the related art, such as bioengineering.

EXAMPLES

Example 1

EGFR Monoclonal Antibody Functionalized TFT

The bio-functionalization enables the exposed ZnO channel direct interaction with the biochemical species being detected. By way of example, the mechanism of detection for an antibody antigen reaction is illustrated in FIG. 2(a)-(d). In the first step (FIG. 2(b)) the unfunctionalized ZnO-bioTFT is positively biased at the drain and gate electrode. The positive voltage at the gate causes the majority carriers of the n-type ZnO channel to accumulate near the base of the ZnO layer to facilitate a conduction path for the current flow from drain to source. The positive voltage at the drain causes sonic of the carriers to also accumulate near the side of the drain electrode forming wedge shaped conduction path. The bias at the drain also acts as an electron pump to drive the current to flow.

For the second step (FIG. 2(c)), the exposed. ZnO channel is functionalized with, for example, EGFR, monoclonal antibodies (mAbs) having free lysine groups. The immobilized antibody molecules caused significant decrease in conductivity of the ZnO surface layer, thus reducing the drain current. Without wishing to be bound by theory, in the third step (FIG. 2(d)), the EGFR protein captured by the EGFR mAbs forms a polarized molecule with a dominant partially-positive charged tip which leads to the accumulation of negative carriers within the ZnO channel to accumulate near the exposed surface where the antibody-protein pairs were present. This carrier accumulation is in addition to the conduction path created near the gate. The combined amount of accumulation layer causes an increase in the current flow. The top molecule layer (reacted protein) acts as a virtual top gate and the antibody layer acts as a virtual insulator layer, thus forming a pseudo-double gated field-effect conduction scheme for the ZnO-bioTFT.

The actual measured drain currents that confirmed each step of the detection process are shown in FIG. 2(a). The drain voltage is fixed to 10V and the gate voltage is varied from –5V to +15V, and the drain current is measured using an HP4156C semiconductor parameter analyzer and Cascade Microtech probe station. Making a reading of the drain current from FIG. 2(a) at a 5V gate voltage, the bare device starts with a current of $8.523 \times 10^{-7}$ A. After the antibodies were immobilized on the exposed ZnO channel, the drain current dropped to $9.097 \times 10^{-11}$ A. After the reaction of 1 pM of EGFR protein with EGFR mAbs, a rise in drain current to $7.818 \times 10^{-9}$ A was detected.

Example 2

Measurement of Different EGFR Solution Concentrations

Figure 3:
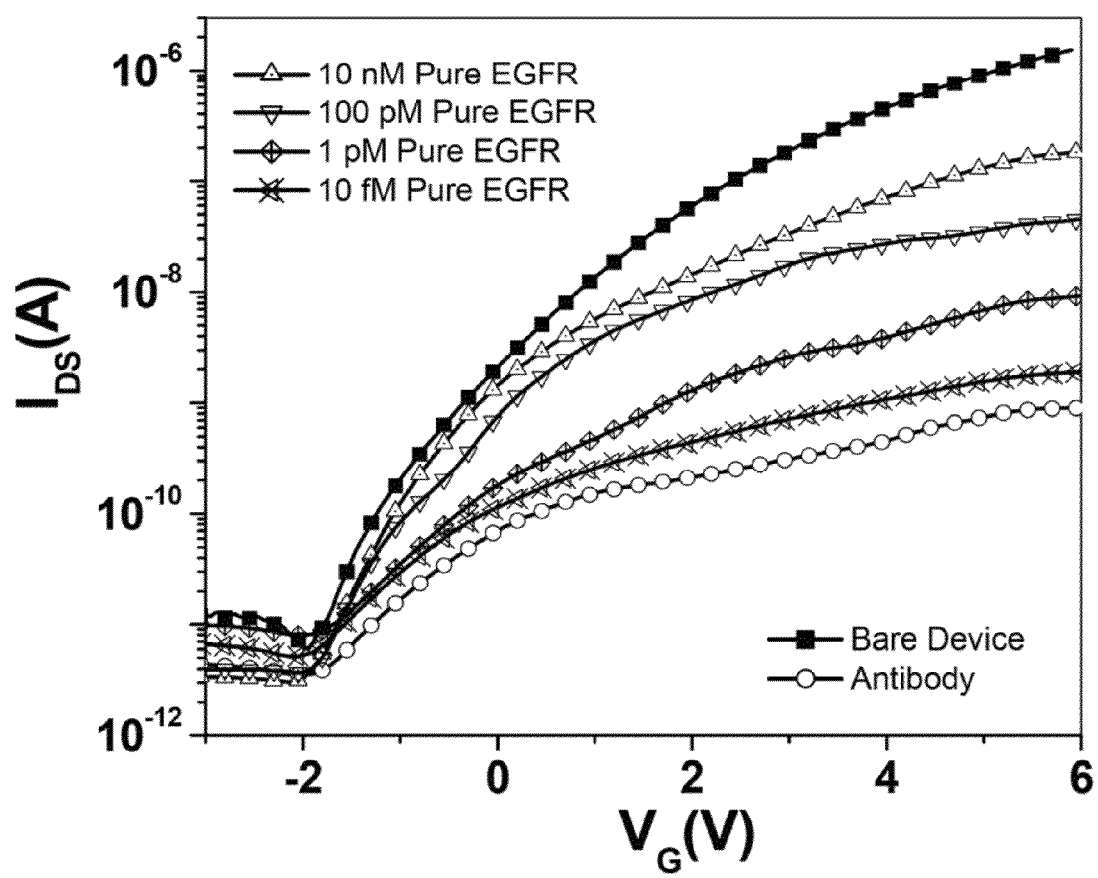
FIG. 3 illustrates drain current versus gate bias for various Molar concentrations of pure EGFR proteins detected by an embodiment ZnO-bioTFT to demonstrate sensitivity.

To demonstrate the high sensitivity of the ZnO-bioTFT, solutions of pure EGFR (in PBS) were prepared with four different Molar concentrations using serial dilutions, each a hundred times more dilute than the previous, namely 10 nM, 100 pM, 1 pM, and finally 10 fM. Each EGFR solution (2 µL) was introduced to a separate but similar ZnO-bioTFT fabricated on a single chip and simultaneously functionalized with EGFR mAbs. The proteins were incubated on the devices for 1 h and washed with PBS (pH 7.4), and dried under nitrogen gas. The drain current was monitored as a function of gate voltage with a fixed drain voltage of 10V, for each concentration. FIG. 3 shows the measured drain current versus gate voltage of the bioTFT. An increase in drain current was measured as the EGFR concentration was increased and the graph also shows that the device was able to detect as low as 10 fM of EGFR concentration, The trend in the current readings agrees with the hypothesis provided by the pseudo-double gating effect discussed above.

Figure 4:
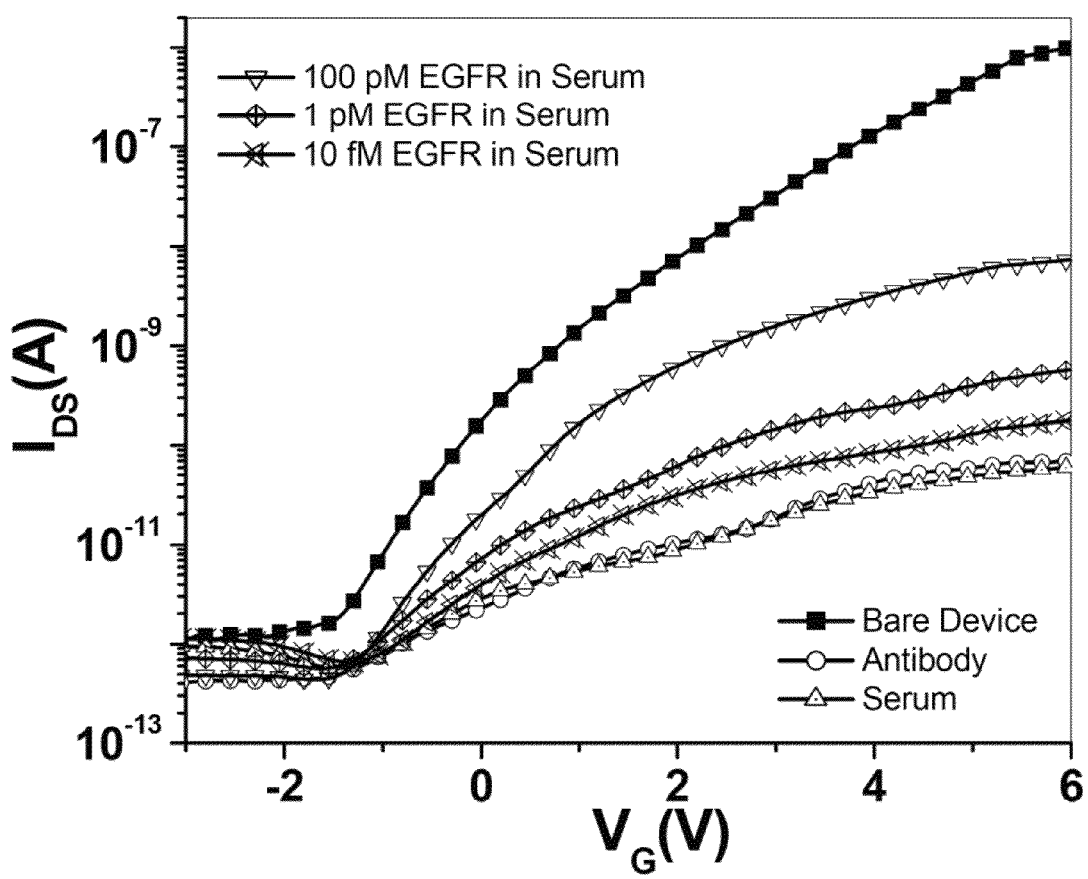
FIG. 4 illustrates drain current versus gate bias for various Molar concentrations of EGFR proteins in a serum solution containing many different proteins.

The highly selective sensing of EGFR using the ZnO-bioTFT was also demonstrated. In another experiment, a 5 mg/ml (in PBS, pH 7.4) goat serum solution was prepared, which contains many different species of proteins. As mentioned above, different EGFR solutions were prepared, namely 100 pM, 1 pM, and 10 fM, using this serum solution and not pure PBS. This method allows the detection of the small amounts of target protein, EGFR, in the presence of a high concentration of serum. For all the concentrations, the total amount of serum present remained approximately the same. Each of the different solutions (2 µL) was introduced onto a chip containing multiple similar bioTFT devices that were bio-functionalized with EGFR mAbs. The drain current of each device was measured as a function of gate voltage, with a fixed drain voltage of 10V. As a control, a serum solution without the EGFR proteins was first introduced to the ZnO-bioTFT. FIG. 4 shows no change in the drain current for the pure serum confirming that there were no EGFR molecules in the solution. The drain current increased as a function of EGFR concentration. The bio-TFT detected only the EGFR proteins out of the many different proteins present in the serum solution introduced onto the sensing, area of the device. Moreover, the device was able to discern as low as 10 fM of EGFR protein concentration in the serum solution.

In summary, embodiment ZnO bioTFT devices have the ability to perform immunosensing with high sensitivity and selectivity. The channel of the bioTFT can be functionalized with amine terminated EGFR monoclonal antibodies. EGFR proteins with the lowest concentration of 10 fM were detected by embodiment devices in both the pure state and selectively in a concentration serum solution containing various other protein species. Embodiment ZnO-bioTFT devices enable bias-controlled operation though the bottom gate configuration. The high sensitivity of embodiment devices is attributed to their high on-off ratio, and the output current trend can be explained by the pseudo-double gating electric field effect. ZnO-bioTFT devices functionalized with EGFR mAbs reacting with EGFR proteins may have potential applications in, for example, cancer diagnosis and treatment.

Example 3

ZnO Resistive Switch for MZO-based 1T1R Integration

The transition metal (TM)-doped ZnO bipolar resistive switching device (R) with ZnO-based thin film transistor (T) into the 1T1R as the basic building, block for the data storage, enabling the reconfigurable operation of the sensors. We have demonstrated the unipolar and bipolar resistive switching devices (see Y. Zhang, Z. Duan, R. Li, C. Ku, P. Reyes, A. Ashrafi and Y. Lu, "FeZnO based resistive switch devices", *TMS & IEEE Journal of Electronic Materials*, 41, 2880 (2012). Due to the differences in the fabrication conditions between the R and T, the fabrication temperature and current density of the resistive switching device (R) is tuned to satisfy the requirement of 1T1R integration. There is close relationship between the compliance current and the RESET current of the R device. The compliance current level is adjusted to limit the LRS current density to match the TFT operation requirement, and reduce the power consumption.

Example 4

System Integration for MZO-Based 2T Sensor Array and 1T1R Data Array

The TFT (T) and resistive switching (R) devices are integrated to form the novel multifunctional bioTFT sensor system on glass or flexible substrates with unique built-in data storage. Two basic building blocks including a sensing unit and a data storage unit is implemented.

Figure 6:
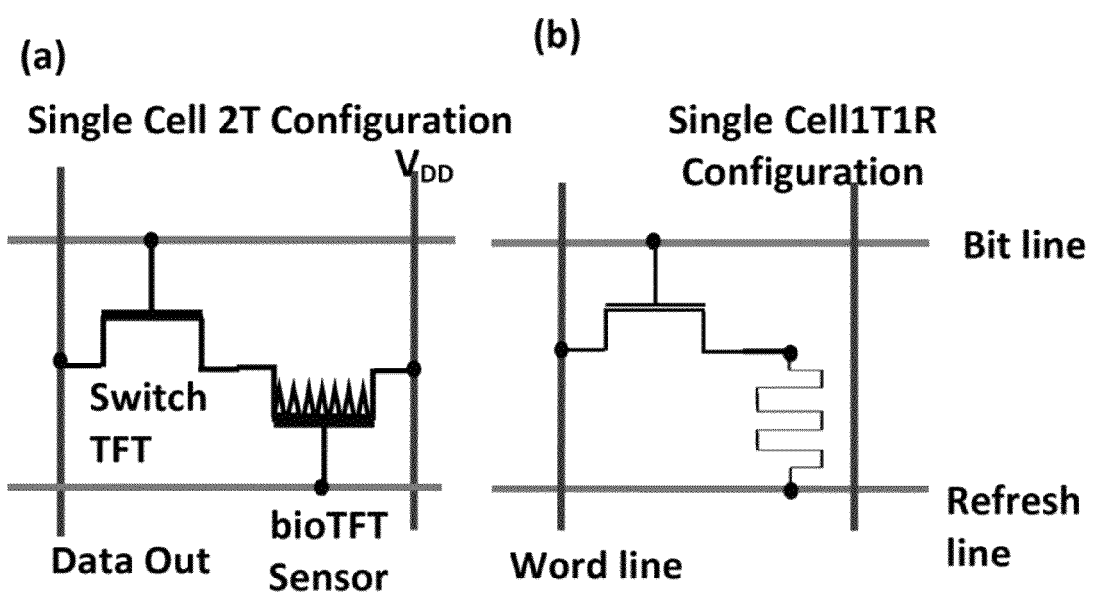
FIG. 6(a) illustrates the embodiment of the single-cell basic building block of the 2-TFT (2T) pair sensor array.
FIG. 6(b) illustrates the embodiment of the single-cell basic building block of the 1T1R nonvolatile memory data storage array.

The 2T BioSensor Array:

The first basic circuit building block is the 2-TFT (2T) single biosensing cell consisting of an addressing TFT and a sensing MZO bioTFT (FIG. 6(a)). In each unit cell, the addressing T enables a biosensing T located in ($X_i$, $Y_i$) of sensing arrays. The bio reaction can be treated as an input gate signal for the MZO bioTFT, which increases the output drain current. The output signal will in turn be stored in another data storage unit, the 1T1R memory arrays. The ZnO-based 1T1R system has great potential for the next generation non-volatile memory application. Each cell includes one ZnO bipolar memristor as the bit cell to store data, and one TFT as the word line (read/write enabling) as shown in FIG. 6(b). The 1T1R array stores data in a non-volatile fashion. Non-volatile data storage ensures that output data of sensing arrays can be stored intact without disturbance of environmental issues. It has to be pointed out that ZnO and MZO based material is one of the most radiation-hard materials, therefore, making it suitable for harsh environmental sensing applications.

Figure 7:
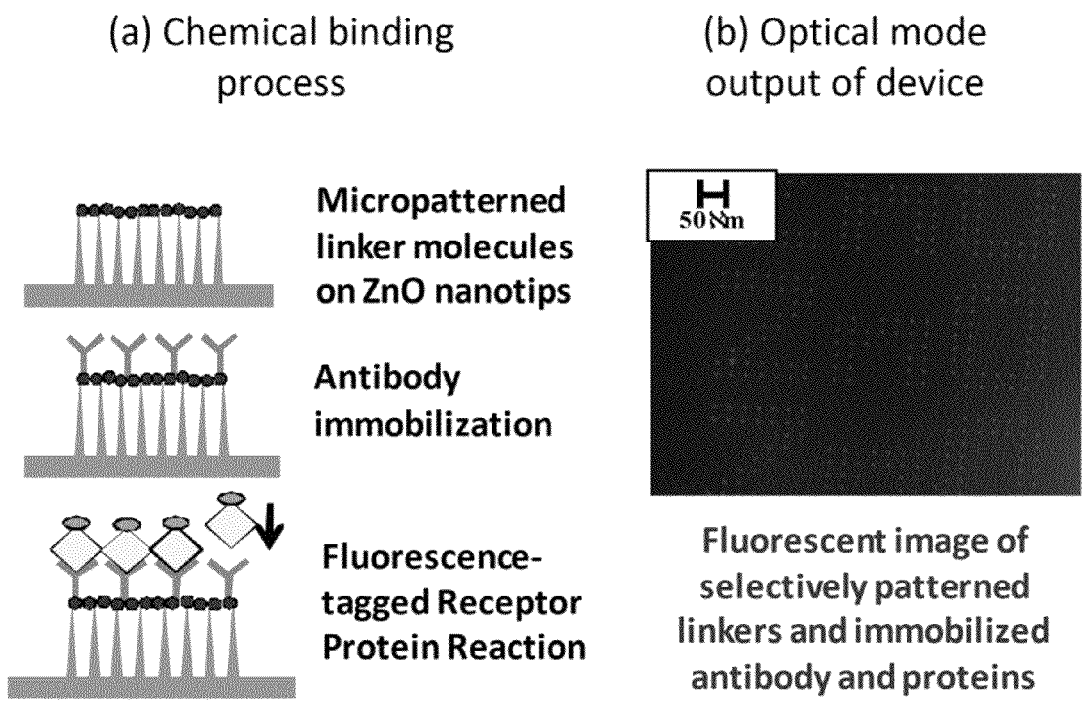
FIG. 7 illustrates optical mode sensing, (a) Biochemical binding process, and (b) optical mode output of device through the fluorescence micrograph of the sensor surface.

Each MZO bioTFT sensor in the array will be enabled (through biofunctionalization) to detect multi-reactions of various biochemical species (enzymes, DNA, protein, antibody etc.). The biochemical detection will be available through dual-mode operations: (a) conductivity variation in each bioTFT cell and the information of the reactions will be stored electronically through the NVM array, and (b) fluorescence micrograph of the sensor array (FIG. 7).

Figure 8:
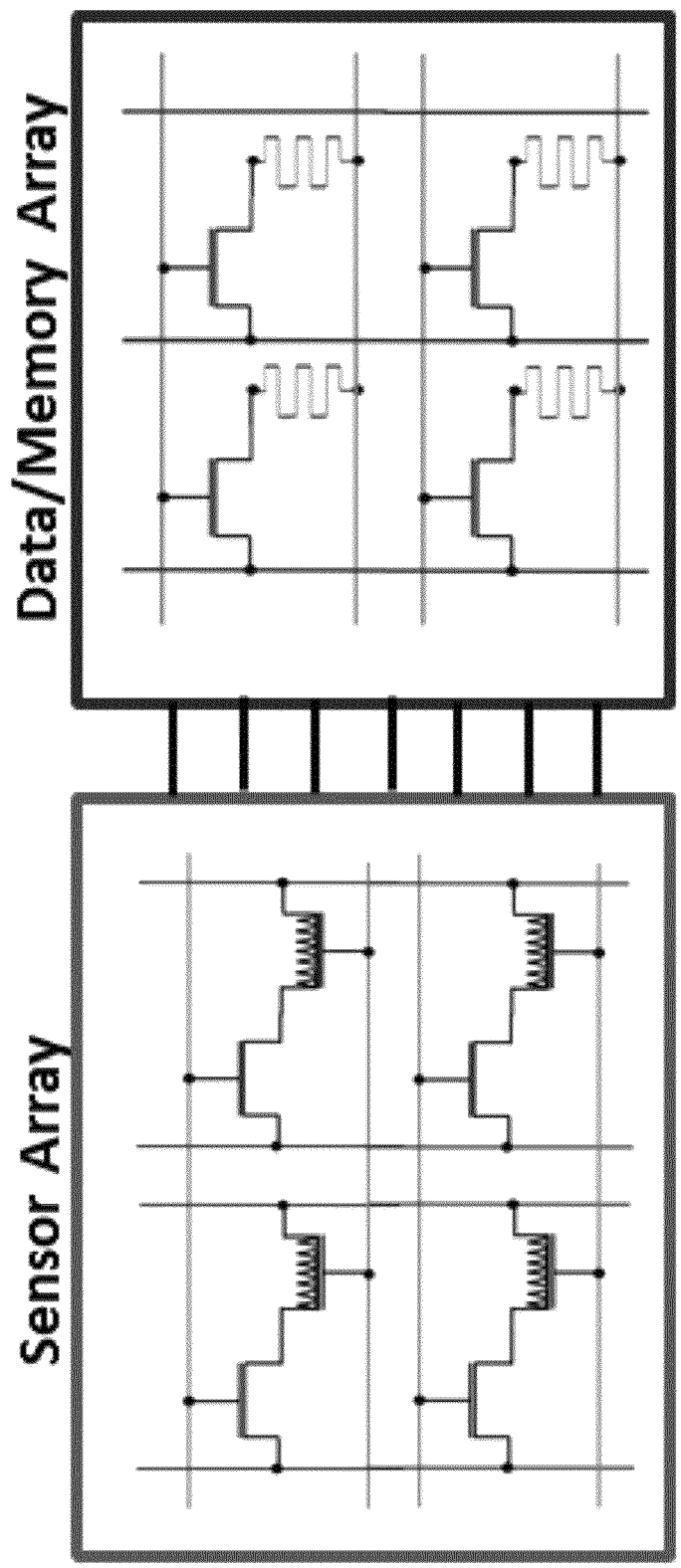
FIG. 8 illustrates the integrated biosensor array system.

The 1T1R NVM Array:

The second basic circuit building block is the 1T1R for the NVM, which enables the built-in data storage. FIG. 6(b) shows the basic single cell configuration of the NVM, The data from each 2T cell in the sensor array which are individually functionalized to bind specifically with different kinds of receptor molecules will be handled by the 1T1R array. This biosensor array will enable a large throughput detection system. Note that a 1T1R cell based on a single material system (ZnO family, including the MZO and Fe-doped ZnO films, ZnO and MZO nanostructures) can effectively simplify the fabrication process to achieve a low-cost, high-speed, non-volatile memory. The low-temperature growth and processing of ZnO-based materials also enable bio-TFTs and 1T1R non-volatile memory systems to be built on glass or flexible substrates. This novel 1T1R non-volatile memory system could also be useful for electronic paper, biosensors, UV detectors, and transparent displays. FIG. 8 shows the integrated sensor system comprising of the 2T biosensor array with the built-in 1T1R NVM data storage array.

Figure 9:
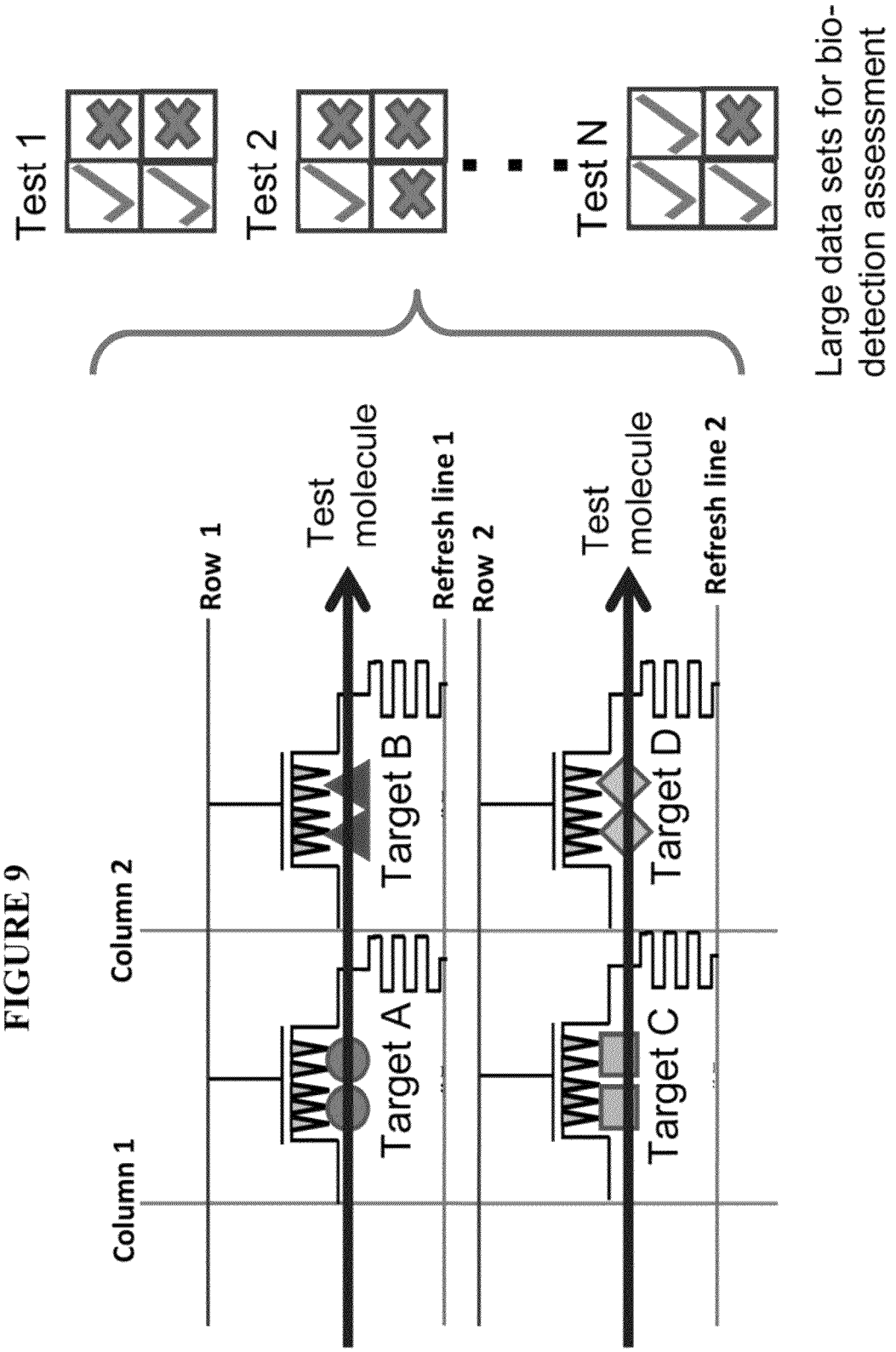
FIG. 9 illustrates the single-shot detection scheme of the integrated biosensor array system.
Figure 10:
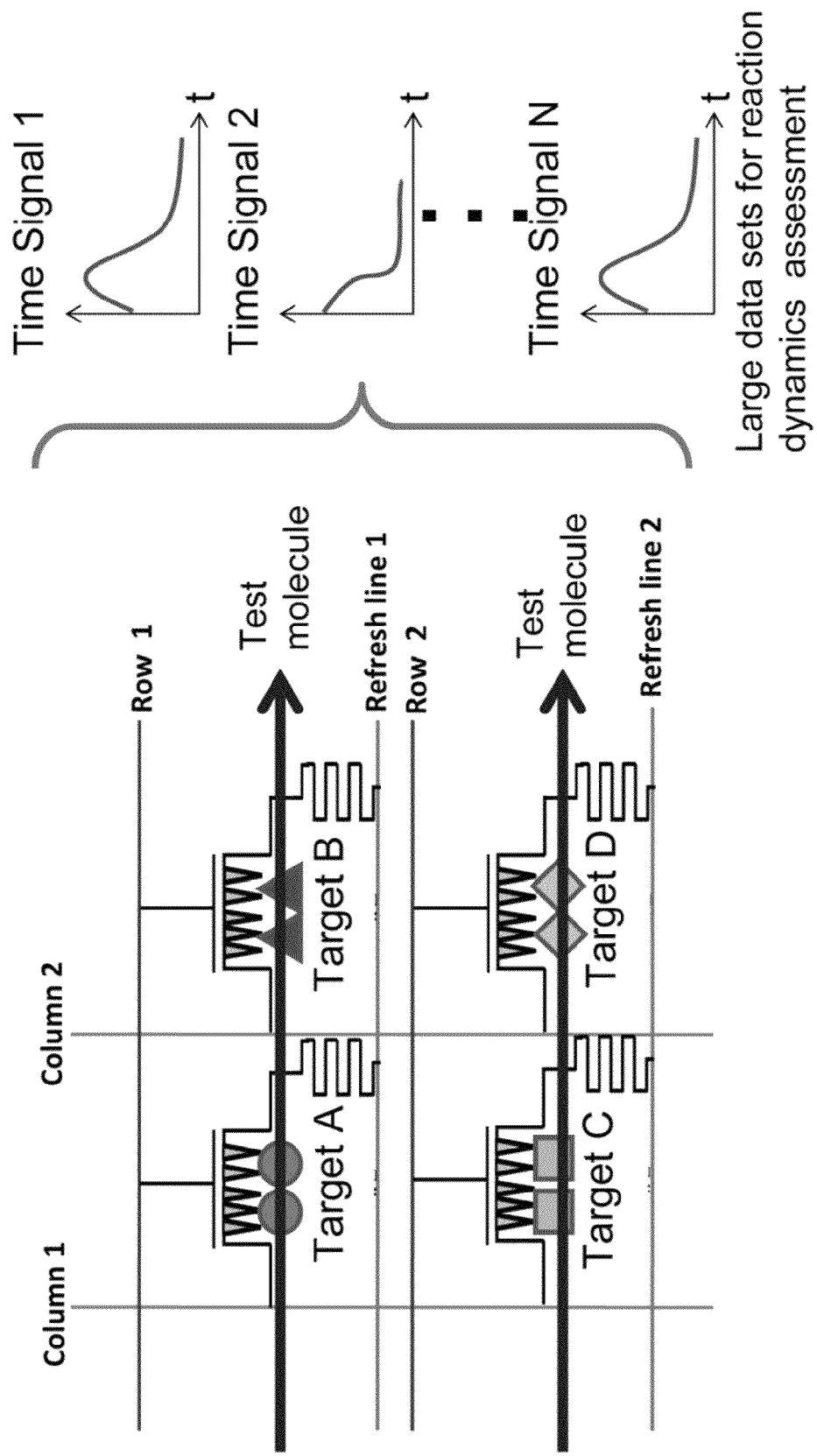
FIG. 10 illustrates the dynamic detection scheme of the integrated biosensor array system.

Data Output Types Various Detections Schemes:

The type of output data depends on the method in which the sensor array is operated. The sensor array will be operated in two different schemes: (a) single-shot detection, and (b) dynamic detection, in the single-shot detection scheme (FIG. 9), each cell in the sensor array will be biofunctionalized, with a different target biomolecule. Then a test solution will be introduced into the entire array and depending on whether the test solution would test positive or negative with the target molecule within each cell, the data will be stored in the memristor. This procedure will be performed for a number of test solutions. Every time one test solution is tested, the array will output its data to the data storage module and will await the other sets of data until all the tests are done. The output data will be a series of matrices of positive/negative test values. This accumulated data will be passed along to the computational module to perform rapid decision-tree type analysis for information processing and decision making. In the dynamic detection scheme (FIG. 10), the same setup will be followed as in the single-shot detection scheme; however, the output data will be continuously monitored and stored in the data module to create an output data series of temporal signals. These signals will give information about the reaction dynamics occurring between the test solution and each target biomolecule.

All publications and references cited in the specification, both patent publications and non-patent publications, are indicative of the level of skill of those skilled in the art to which this invention pertains. All these publications and references are herein fully incorporated by reference to the same extent as if each individual publication or reference were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A zinc oxide-based thin film transistor biosensor (ZnO-bioTFT sensor), comprising a ZnO-based thin film transistor (TFT) built on a substrate, wherein said ZnO-TFT has a bottom-gate TFT configuration, said bottom-gate TFT comprising an exposed top channel layer made of a ZnO-based material, said ZnO-based material comprising an undoped or doped $Mg_xZn_{1-x}O$ (MZO) film, and wherein said exposed top channel layer is biofunctionalized with a linker layer comprising at least one ligand having an affinity for a biomarker.

2. The ZnO-bioTFT sensor of claim 1, wherein said bottom-gate TFT configuration further comprises a pseudo top-gate formed by the linker layer and an attached biomarker, thereby produces a configuration having a double-gating effect.

3. The ZnO-bioTFT sensor of claim 1, wherein the substrate is a rigid solid-state material.

4. The ZnO-bioTFT sensor of claim 3, wherein the rigid solid-state material is selected from silicon or glass.

5. The ZnO-bioTFT sensor of claim 1, wherein the substrate is a flexible material.

6. The ZnO-bioTFT sensor of claim 5, wherein said flexible material is selected from a polymer or paper material.

7. The ZnO-bioTFT sensor of claim 1, wherein the ZnO-based material is an intrinsic (undoped) or extrinsic (doped) ZnO film.

8. A zinc oxide-based thin film transistor biosensor (ZnO-bioTFT sensor), comprising a ZnO-based thin film transistor (TFT) built on a substrate, wherein said ZnO-TFT has a bottom-gate TFT configuration, said bottom-gate TFT comprising an exposed top channel layer made of a ZnO-based material, wherein said ZnO-based material is an intrinsic or extrinsic (doped or alloyed) ZnO film, and wherein the ZnO film is modified by deposition of a layer of ZnO-based nanostructures on top of it.

9. The ZnO-bioTFT sensor of claim 8, wherein said nanostructures have the controlled surface wettability state of super-hydrophilicity so that said ZnO-bioTFT sensor reduces liquid sample consumption and significantly enhances the sensitivity of the TFT sensor.

10. The ZnO-bioTFT sensor of claim 8, wherein the ZnO-based nanostructures have a controlled morphology selected from flat, rough, and sharp tip end, to enhance binding affinity with different bio-species, thereby increasing the sensitivity and selectivity of said ZnO-bioTFT sensor.

11. A zinc oxide-based thin film transistor biosensor (ZnO-bioTFT sensor), comprising a ZnO-based thin film transistor (TFT) built on a substrate, wherein said ZnO-TFT has a bottom-gate TFT configuration, said bottom-gate TFT comprising an exposed top channel layer made of a ZnO-based material, and wherein the ZnO-based material of said channel layer comprises an undoped or doped $Mg_xZn_{1-x}O$ ($0 \leq x \leq 0.06$) (MZO) film.

12. The ZnO-bioTFT sensor of claim 11, wherein the MZO-based material of said channel layer is further modified with MZO-based nano structures deposited thereon with controlled surface morphology and wettability.

13. The ZnO-bioTFT sensor of claim 12, wherein the MZO-based nanostructures have a super-hydrophilic state of surface wettability that significantly reduces liquid sample consumption and increases the sensitivity of said bio-TFT device.

14. The ZnO-bioTFT sensor of claim 12, wherein the MZO-based nano-structures have a controlled morphology, selected from flat, rough, and sharp tip end, to enhance binding with different bio-species and enhance the sensitivity and selectivity of the TFT sensor.

15. A 2T biosensor array comprising a 2T basic cell formed from a first ZnO-bioTFT sensor integrated with a second addressing ZnO-TFT, wherein said first ZnO-bioTFT sensor and said second addressing ZnO-TFT are configured that said first ZnO-bioTFT sensor is enabled by said second addressing ZnO-TFT, and wherein said first ZnO-bioTFT sensor and said second addressing ZnO-TFT each comprises a ZnO-based thin film transistor (TFT) built on the same substrate, and said first ZnO-bioTFT sensor and said second addressing ZnO-TFT each has a bottom-gate TFT configuration, said bottom-gate TFT comprising an exposed top channel layer made of a ZnO-based material, wherein said exposed top channel layer of said first ZnO-bioTFT sensor further comprises a biofunctionalized linker layer.

16. A 2T biosensor array comprising multimode sensing operations and a 2T basic cell formed from a first ZnO-bioTFT sensor integrated with a second addressing ZnO-TFT, wherein said first ZnO-bioTFT sensor and said second addressing ZnO-TFT each comprises a ZnO-based thin film transistor (TFT) built on the same substrate, and said first ZnO-bioTFT sensor and said second addressing ZnO-TFT each has a bottom-gate TFT configuration, said bottom-gate TFT comprising an exposed top channel layer made of a ZnO-based material, wherein said exposed top channel layer of said first ZnO-bioTFT sensor further comprises a biofunctionalized linker layer, and wherein said multimodes comprise electrical mode and optical mode.

17. The 2T biosensor array of claim 16, wherein the sensing operation of said electrical mode provides an electrical signal output and said sensing operation of said optical mode provides a fluorescence image output signal.

18. A 1T1R-based nonvolatile memory (NVM) array, comprising a ZnO-TFT (T) and a ZnO-based resistive switch (R), wherein the ZnO-TFT (T) and the ZnO-based resistive switch (R) are integrated to form a ZnO-based 1T1R basic unit cell configuration, and wherein said ZnO-TFT comprises a ZnO-based thin film transistor (TFT) built on a substrate, and said ZnO-TFT has a bottom-gate TFT configuration, and said bottom-gate TFT comprising an exposed top channel layer made of a ZnO-based material.

19. An integrated bioTFT (IBTFT) sensor system, comprising:
(1) a 2T biosensor array comprising a 2T basic cell formed from a first ZnO-bioTFT sensor integrated with a second addressing ZnO-TFT,
wherein said first ZnO-bioTFT sensor and said second addressing ZnO-TFT are configured that said first ZnO-bioTFT sensor is enabled by said second addressing ZnO-TFT, and
wherein said first ZnO-bioTFT sensor and said second addressing ZnO-TFT each comprise a ZnO-based thin film transistor (TFT) built on a substrate, and said first ZnO-bioTFT sensor and said second addressing ZnO-TFT have the same bottom-gate TFT configuration with the same exposed top channel layer made of a ZnO-based material, wherein said exposed top channel layer of said first ZnO-bioTFT sensor further comprises a biofunctionalized linker layer, and
said 2T biosensor array integrated with
(2) a built-in data storage 1T1R NVM array comprising
(a) a ZnO-based thin film transistor (T) built on a substrate, wherein said ZnO-TFT has a bottom-gate TFT configuration, said bottom-gate TFT comprising an exposed top channel layer made of a ZnO-based material, and
(b) a ZnO-based resistive switch (R),
wherein the ZnO-TFT (T) and the ZnO-based resistive switch (R) are integrated to form a ZnO-based 1T1R basic unit cell configuration.

20. The integrated bioTFT (IBTFT) sensor system of claim 19, wherein said 2T biosensor array and said 1T1R NVM array are on the same substrate.

* * * * *